(12) United States Patent
Brandenburger et al.

(10) Patent No.: US 9,108,031 B2
(45) Date of Patent: Aug. 18, 2015

(54) CONNECTOR HAVING A MEMBRANE, FOR CONNECTING A SYRINGE TO A CONTAINER OR TUBING

(75) Inventors: Torsten Brandenburger, Reichelsheim (DE); Ismael Rahimy, Friedberg (DE)

(73) Assignee: FRESENIUS KABI DEUTSCHLAND GMBH, Bad Homburg (DE)

( * ) Notice: Subject to any disclaimer, the term of this patent is extended or adjusted under 35 U.S.C. 154(b) by 564 days.

(21) Appl. No.: 13/061,602

(22) PCT Filed: Sep. 23, 2009

(86) PCT No.: PCT/EP2009/006851
§ 371 (c)(1),
(2), (4) Date: Mar. 1, 2011

(87) PCT Pub. No.: WO2010/034470
PCT Pub. Date: Apr. 1, 2010

(65) Prior Publication Data
US 2011/0166532 A1 Jul. 7, 2011

(30) Foreign Application Priority Data
Sep. 25, 2008 (DE) .......................... 10 2008 048 988

(51) Int. Cl.
*A61M 39/16* (2006.01)
*A61M 39/10* (2006.01)
(Continued)

(52) U.S. Cl.
CPC ............ *A61M 39/045* (2013.01); *A61J 1/2096* (2013.01); *A61M 39/16* (2013.01);
(Continued)

(58) Field of Classification Search
CPC .............. A61M 2039/0288; A61M 2039/027; A61M 2039/0276; A61M 2039/0273; A61M 2039/009; A61M 2039/0036; A61M 39/10; A61M 39/14; A61M 39/1011; A61M 39/16
USPC .................................. 604/403, 256, 201, 249
See application file for complete search history.

(56) References Cited

U.S. PATENT DOCUMENTS 5,215,538 A * 6/1993 Larkin ........................... 604/249
5,806,831 A * 9/1998 Paradis ....................... 251/149.1
(Continued)

FOREIGN PATENT DOCUMENTS

| DE | 19728755 | 1/1999 |
| DE | 10348016 | 6/2005 |

(Continued)

OTHER PUBLICATIONS

See definiition of "break off". Merriam-Webster's Collegiate Dictionary: Eleventh Edition. 2004.*

*Primary Examiner* — Aarti B Berdichevsky
*Assistant Examiner* — Matthew A Engel
(74) *Attorney, Agent, or Firm* — Occhiuti & Rohlicek LLP

(57) ABSTRACT

The invention relates to a device for connecting a syringe to a container or tubing, particularly for connecting a syringe to a container for receiving infusion-, transfusion-, or enteral nutrition solutions and particularly for connecting a syringe to tubing of a blood tube system of an extracorporeal blood treatment device or to tubing for a venous portal. The invention also relates to a container and tubing with such a device. The device according to the invention has a connecting part (2) which connects to the container or the tubing, the connecting part having a recess (3) in which a membrane (12) is arranged, the membrane closing the channel-shaped recess. A hollow body (22) having a syringe (23) is arranged in the recess (3) of the connecting part (2) in such a manner that the membrane (12) is pierced upon connection of the syringe to the connecting part. The device according to the invention is characterized in that the membrane (12) is arranged above the hollow body (22) in the connecting part (2) recess (3), such that upon connection of the syringe to the connecting part, the membrane is pressed onto the tip of the hollow body.

19 Claims, 7 Drawing Sheets

(51) Int. Cl.
  *A61M 39/04* (2006.01)
  *A61J 1/20* (2006.01)
  *A61M 39/20* (2006.01)
  *A61M 39/26* (2006.01)

(52) U.S. Cl.
  CPC .............. *A61M 39/20* (2013.01); *A61M 39/26*
      (2013.01); *A61J 2001/2044* (2013.01); *A61M*
      *39/1011* (2013.01); *A61M 2039/1061*
      (2013.01); *A61M 2039/1072* (2013.01)

(56) References Cited

U.S. PATENT DOCUMENTS

| | | | |
|---|---|---|---|
| 7,815,614 B2* | 10/2010 | Fangrow, Jr. | 604/256 |
| 7,857,802 B2 | 12/2010 | Brandenburger et al. | |
| 7,981,090 B2* | 7/2011 | Plishka et al. | 604/249 |
| 7,998,134 B2* | 8/2011 | Fangrow et al. | 604/535 |
| 8,211,069 B2* | 7/2012 | Fangrow, Jr. | 604/256 |
| 2004/0092886 A1 | 5/2004 | Mayer | |
| 2004/0227120 A1 | 11/2004 | Raybuck | |
| 2006/0157971 A1 | 7/2006 | Baldwin | |
| 2006/0264891 A1* | 11/2006 | Lopez | 604/500 |
| 2006/0264892 A1* | 11/2006 | Lopez | 604/500 |
| 2007/0017583 A1* | 1/2007 | Fangrow, Jr. | 137/614.06 |
| 2007/0060902 A1* | 3/2007 | Brandenburger et al. | 604/403 |

FOREIGN PATENT DOCUMENTS

| | | |
|---|---|---|
| EP | 0309771 | 4/1989 |
| EP | 0681493 | 6/2000 |
| WO | 98/50106 | 11/1998 |
| WO | 2005/037362 | 4/2005 |

* cited by examiner

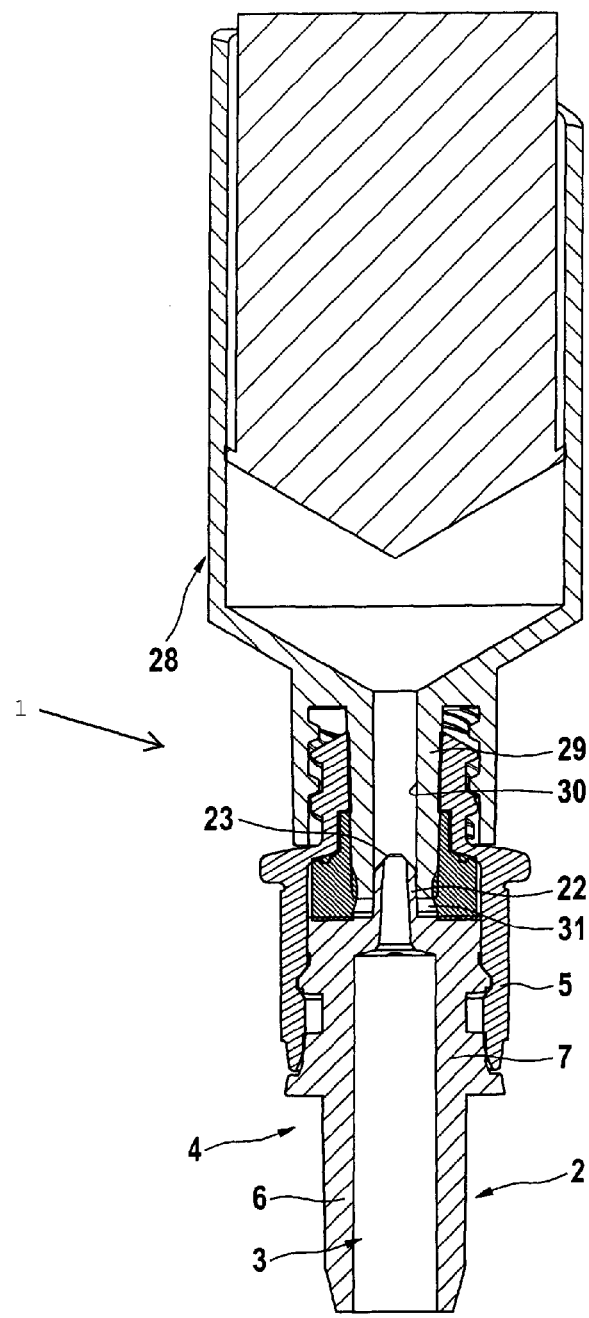
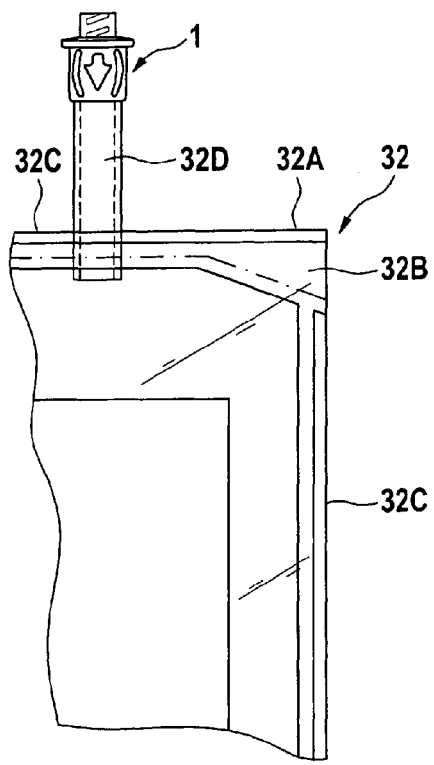
Fig. 6
Fig. 7

CONNECTOR HAVING A MEMBRANE, FOR CONNECTING A SYRINGE TO A CONTAINER OR TUBING

CROSS-REFERENCE TO RELATED APPLICATIONS

This application is the National Stage of International Application No. PCT/EP2009/006851, filed on Sep. 23, 2009, which claims the priority of German Patent Application No. 10 2008 048 988.3, filed on Sep. 25, 2008. The contents of both applications are hereby incorporated by reference in their entirety.

FIELD OF INVENTION

The invention relates to a connector for connecting a syringe to a container or tubing, in particular for connecting a syringe to a container for holding infusion, transfusion or enteral nutrient solutions, and in particular for connecting a syringe to tubing of a blood tube system of an extracorporeal blood treatment device or tubing for venous access. Furthermore, the invention relates to a container and to tubing with a connector of this type.

BACKGROUND

DE-A-197 28 775 describes an infusion bag with an injection part and a withdrawal part. The injection part is intended for delivery of a medicament by means of an injection syringe, whereas the withdrawal part is used for withdrawing the solution by means of a spike. The injection and withdrawal parts have a tubular connecting part that is sealed by a protective cap designed as a break-off part.

Tapered connections having a tapered stem and a tapered sleeve, the tapered surfaces of which are standardized, are known in medical technology for connecting medical implements. The tapered connections that are not lockable and have standardized tapered surfaces are referred to as Luer connectors and the lockable tapered connections are referred to as Luer lock connectors. The Luer connectors or Luer lock connectors with a tapered shaft are referred to as male connectors and connectors with a tapered sleeve are referred to as female connectors.

An infusion bag with connectors for delivering and withdrawing liquids is also known from DE-A-103 48 016. The connector for delivering a liquid permits connection of a conventional syringe to a tapered connection, in particular a Luer lock tapered connection, which does not have an injection needle. Since an injection needle having a small cross section is not required, relatively viscous active substances can also be injected rapidly. There is no risk of injury to the nursing staff. There is also no risk of the infusion bag being damaged. The possibility of screwing together the syringe and the connector ensures that the connection does not become detached. The connector has a self-sealing, slit membrane that is pierced by the tapered shaft of the syringe. After the tapered shaft is pulled out, the membrane closes again and therefore prevents the liquid from running out of the bag. The connector has proven successful in practice. However, a requirement for correct functioning of the known connector is that the membrane can open easily and reliably.

EP-A-0 681 493 describes a connector for connecting a syringe. However, the connector is based on a different functioning principle from the connector described above. The known connector has a hollow pin that is arranged within a stopper tightly sealing the connector. The pin has a plurality of lateral openings below its point. When the syringe is connected to the connector, the stopper surrounding the pin is displaced by the tapered shaft of the syringe such that the pin penetrates the tapered shaft. A liquid connection is therefore produced between the syringe and the connector via the lateral openings of the pin.

EP 0 309 771 A1 describes a device for injecting liquids into a channel of a cannula connecting piece. The device has a membrane that is pierced by a cannula upon connection of the cone of a syringe. In this case, the basic principle involves the tapered shaft of the syringe taking hold of a clamping sleeve that surrounds the membrane and is supported on a lower flange of the membrane. As a result, the membrane is pushed over the cannula. The production and assembly of the known device is relatively costly and complicated because of the additional clamping sleeve.

U.S. Pat. No. 7,396,051 B2 describes an arrangement of connectors, in which a membrane of one connector is penetrated by a hollow body, the hollow body advancing into a cylindrical body of the other connector. However, the cylindrical body is not the cone of a syringe.

SUMMARY OF THE INVENTION

The invention is based on the object of providing a connector that permits simple connection of a syringe to a container or to tubing without the risk of injury, wherein the connector securely seals the container or the tubing after removal of the syringe.

Furthermore, it is an object of the invention to provide a container or tubing with a connector permitting simple connection of a syringe to the container or the tubing without the risk of injury.

Advantageous embodiments of the invention are the subject matter of the dependent claims. In some embodiments, the connector has a connecting part that is to be connected to the container or the tubing and that has a recess in which a membrane, with which the recess is closed, is arranged. Furthermore, a hollow body with a point is arranged in the recess of the connecting part in such a manner that the membrane is pierced when the syringe is connected to the connecting part.

The connector according to the invention is distinguished at least in part because at least that part of the membrane that is pierced is arranged above the hollow body in the recess of the connecting part and therefore, when the syringe is connected to the connecting part, that part of the membrane that is to be pierced is pressed onto the point of the hollow body. The effect achieved by this is that the membrane can be easily and reliably pierced without there being the risk of twisting the membrane.

In the arrangement according to the invention of the syringe with the tapered shaft and the connector for connecting the syringe to a container or tubing, the tapered shaft of the syringe and the hollow body are arranged in such a manner that the tapered shaft of the syringe is sealed in relation to the hollow body when the syringe is connected to the connector. When the syringe is connected to the connecting part, the point of the syringe presses the membrane directly onto the hollow body. In the process, the point of the syringe acts directly on the membrane.

When the syringe is connected to the connector, the tapered shaft of the syringe is not only sealed in relation to the hollow body but also in relation to the connecting part having the preferably conical connecting piece of the connector such that both parts are securely sealed off from each other. This is crucial in particular when administering cytostatics.

Since the point of the syringe is advantageously arranged at a distance from the preferably slit membrane, unintentional opening of the membrane is prevented even if the two containers with the connector are to be sterilized, in which case there would otherwise be a risk of the membrane being deformed because of the positive pressure arising in the container.

In a preferred embodiment, at least that part of the membrane that is pierced and the hollow body are arranged at a distance from each other in the recess of the connecting part. However, it is in principle also possible for the point of the hollow body to come into contact with the membrane. The sole crucial factor is to ensure that the membrane is not damaged by the point of the hollow body before the syringe is connected to the connecting part.

In a particularly preferred embodiment, the hollow body, with which the membrane is pierced is a cannula with a ground section. Consequently, the hollow body does not need to have any lateral openings or slits. The liquid can flow in the axial direction into the lumen of the cannula.

Another particularly preferred embodiment makes provision for the hollow body in the recess of the connecting part to be fastened to a disk-shaped body that preferably has openings. The openings in the disk-shaped body are preferably bores distributed circumferentially around the hollow body. This preferred embodiment has the advantage that the container to which the connector is connected can be filled through the openings. Another advantage is that, when required, injection of additional liquids, for example insulin or heparin, by a syringe with an injection needle (cannula) is in principle possible, optionally even directly through the openings.

The membrane is preferably slit in order to maintain a seal while receiving the tapered shaft of a syringe. This facilitates the piercing of the self-sealing membrane, in particular by a hollow body composed of plastic. After the tapered shaft of the syringe has been pulled out, the membrane can be closed again, and therefore liquid is prevented from running out of the container or the tubing. However, it is also possible for the membrane not to be slit, in particular if the hollow body is a pin, and in particular, a metal pin.

The connecting part preferably has an external thread for connection of a Luer lock syringe that can be screwed securely to the connecting part. However, it is also possible that the connecting part does not have an external thread, and therefore that only a Luer syringe without a screw thread can be connected.

In a particularly preferred embodiment, the connecting part is composed of an upper subsection and a lower subsection that are fixed by clicking into place. In this embodiment, for the fastening of the hollow body, the disk-shaped body is preferably arranged at the upper end of the lower subsection. The membrane is preferably held clamped between the upper and lower subsections. This facilitates the assembly. However, the connecting part may also be a single piece.

The membrane preferably has an upper, plate-like portion that is adjoined by an annular, lower portion. In this embodiment, the lower, annular portion of the membrane is preferably held clamped between the upper and lower subsections of the connecting part, whereas the plate-like portion is completely pierced by the point of the hollow body upon connection of the syringe.

Preferably, the upper side of the membrane has a trough-shaped depression that ensures that the tapered shaft of the syringe is reliably guided and that also ensures that the membrane is reliably sealed after the tapered shaft has been pulled out.

The recess-closing break-off part of the connector according to the invention is advantageously designed as a flat gripping piece in order to be able to be held by the thumb and index finger, thus simplifying its handling. The break-off part can be connected to the connecting part of the connector via an annular breaking zone. As a result, although the break-off part has a secure grip, it can nevertheless be detached relatively easily.

The connector according to the invention is expediently an injection-molded part that can be produced cost-effectively in large piece numbers.

According to the invention, the container for medicinal liquid is connected to the connector. For this purpose, the connecting part of the connector may differ in design. Adhesive bonds and/or welding connections are possible. The container may be a bag, in particular an infusion or transfusion bag, or a bag for holding an enteral nutrient solution, with it being possible for the connecting part to be designed as a closure part that is to be welded or adhesively bonded to the bag. However, the container may also be a bottle, with it being possible for the connector to be designed as a closure cap or for the connecting part of the connector to be designed as an adapter for the closure of a bottle.

The tubing for medicinal liquids is distinguished in that the connector is connected to the tubing. The tubing may be, for example, part of a blood tube system of an extracorporeal blood treatment device or tubing for venous access.

BRIEF DESCRIPTION OF THE DRAWINGS

A number of exemplary embodiments of the invention are explained in more detail below with reference to the drawings, in which:

FIG. 6 shows the connector from FIGS. 1 to 5 with a connected syringe in a sectioned illustration, FIG. 7 shows an infusion or transfusion bag with the connector in a partially sectioned illustration.

DETAILED DESCRIPTION

Figure 1:
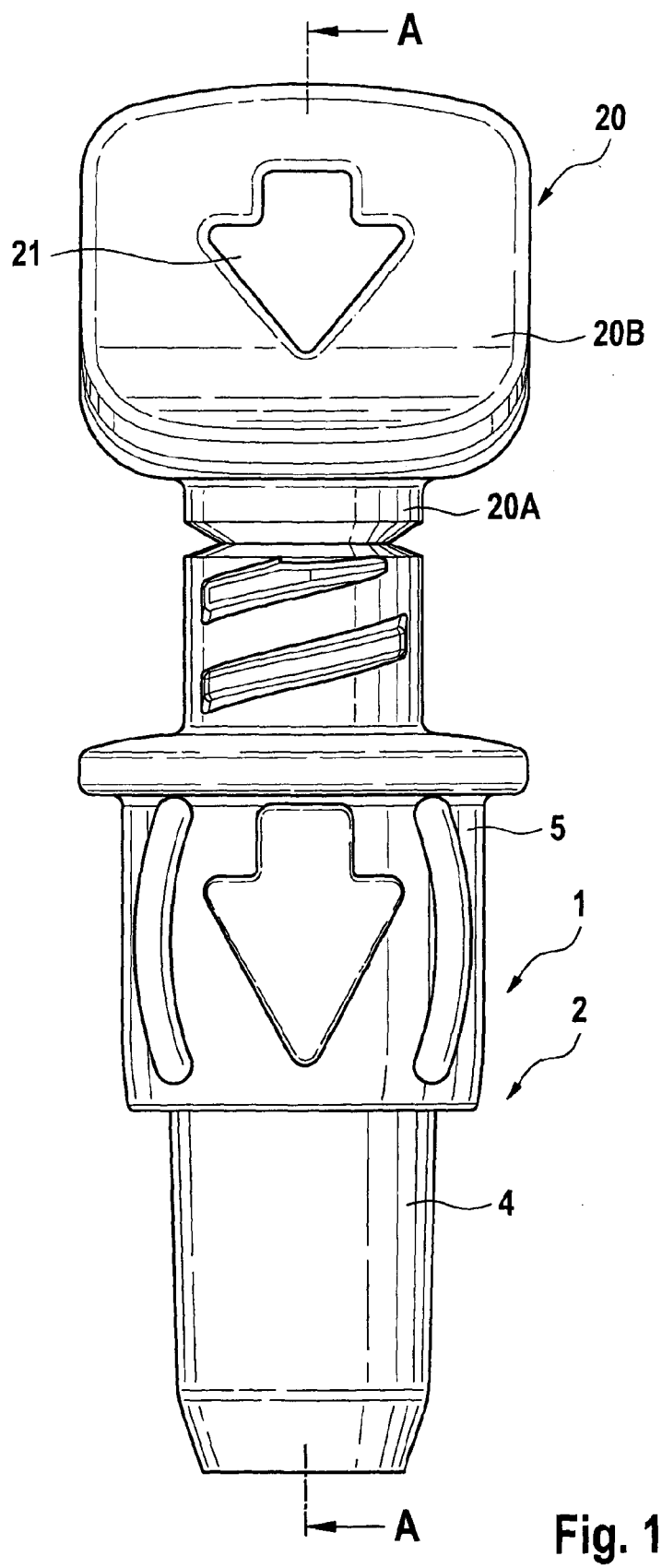
FIG. 1 shows an exemplary embodiment of the connector according to the invention in side view.
Figure 2:
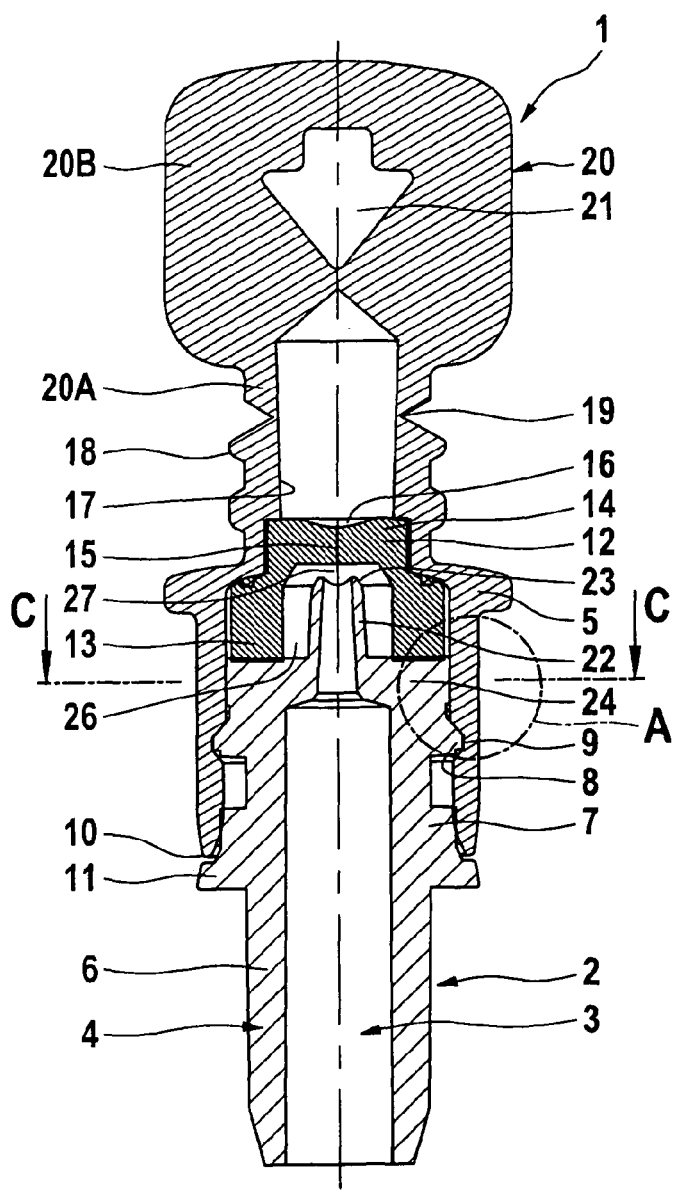
FIG. 2 shows a section through the connector from FIG. 1 along the line A-A.

FIGS. 1 to 6 show a first exemplary embodiment of a connector 1 according to the invention. The connector 1 connects a syringe to a container. FIG. 1 shows a side view of the connector 1. FIG. 2 shows the same connector 1 in cross-section. In both FIGS. 1 and 2, no syringe has been connected to the connector 1.

The connector 1 is designed as an injection part for injecting an active substance into a container that contains a medicinal liquid. A typical container is infusion bag. Another typical container is a transfusion bag.

The connector 1, which is an injection molded part made of polypropylene, has a connecting part 2 with a channel-shaped recess 3, best seen in FIG. 2. The connecting part 2 is composed of a bag-side lower subsection 4 and a connection-side upper subsection 5. The bag-side lower subsection 4 of the connecting part 2 has a lower portion 6 and an upper portion 7, both of which are substantially cylindrical. The lower portion 6 has a smaller external diameter than the upper portion 7. The lower portion 6 can be inserted or pushed into and either welded to or adhesively bonded to a connecting piece of a film bag. However, the lower portion 6 of the bag-side lower subsection 4 of the connecting part 2 may also be welded or adhesively bonded directly into the film bag without a connecting piece.

The lower and upper subsections 4, 5 of the connecting part 2 are connected to each other by being clicked into place. For this purpose, the outer wall of the upper portion 7 of the lower subsection 4 of the connecting part 2 has an encircling extension 8. When the lower subsection 4 and the upper subsection 5 are pressed together, the encircling extension 8 clicks into an encircling groove 9 on an inner wall of the upper subsection 5 of the connecting part 2. An encircling projection 11 at a lower end of the upper portion 7 of the lower subsection 4 supports a lower edge 10 of the upper subsection 5.

A self-sealing membrane 12 composed of an elastic material, also referred to as a septum, is held clamped with elastic deformation between the lower and upper subsections 4, 5 of the connecting part 2. The self-sealing membrane 12 has an annular, lower portion 13 that is clamped between the lower and upper subsections 4, 5 of the connecting part 2. The lower, annular portion 13 of the membrane 12 adjoins an upper, plate-like portion 14. In the center of the plate-like portion 14, the membrane 12 has a continuous slit 15. In some embodiments, the membrane 12 has just one transversely running slit 15. Other embodiments have a crosswise slit 15 or a star-shaped slit 15. The slit 15 preferably extends virtually over the entire cross section of the plate-like portion 14 of the membrane 12. On the upper side of the plate-like portion 14, the membrane 12 has a trough-shaped depression 16 in the center.

Above the membrane 12, the connecting part 2 is designed as a connecting piece that has an internal cone 17 and an external thread 18. The internal cone 17 and external thread 18 correspond to the tapered shaft of a Luer lock tapered connection of a conventional Luer lock syringe. Therefore, the tapered shaft of the Luer lock syringe can be pushed into the internal cone 17 of the connecting piece in a sealing manner and can be screwed securely to the connecting part 2.

A cap-shaped break-off part 20, which closes the channel-shaped recess 3 of the connecting part 2, adjoins the connecting piece 2 of the connector 1 via an annular breaking zone 19. The break-off part 20, which forms a tamper-evident closure for the connector 1, has a lower, rotationally symmetrical base part 20A and an upper, flat gripping piece 20B. A cut-out 21 in the flat gripping piece 20B forms a downwardly pointing arrow that identifies the connector 1 as an injection part.

Upon connection of a Luer lock syringe to the connector 1, the membrane 12 is pierced. For this purpose, the connector 1 has a hollow body that defines a cannula 22 having a point 23.

Figure 5:
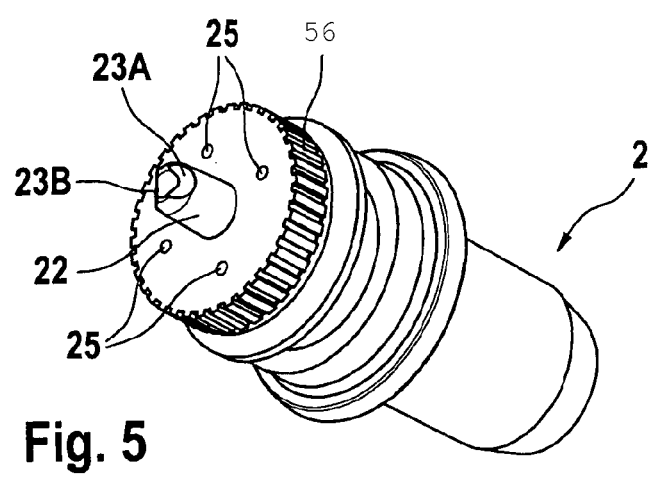
FIG. 5 shows the lower subsection of the connector in a perspective illustration.

The cannula's point 23 has a ground section that has two mutually opposite, lateral ground surfaces 23A and 23B, as shown in FIG. 5.

The sharpened cannula 22 is fastened to a center of a disk-shaped body 24 that is integrally formed on an upper end of the lower subsection 4 of the connecting part 2. The disk-shaped body 24 has a plurality of bores 25 that are distributed circumferentially around the cannula 22, as shown in FIG. 5.

The cannula 22 extends from the disk-shaped body 24 of the lower subsection 4 of the connecting part 2 into a first cylindrical recess 26 that is enclosed by the lower, annular portion 13 of the membrane 12. In this case, only a narrow gap 27 remains between a lower side of the upper, plate-like portion 14 of the membrane 12 and the point 23 of the cannula 22.

Figure 3:
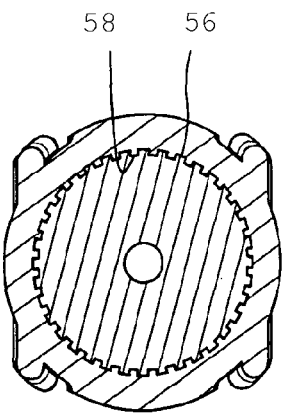
FIG. 3 shows a section through the connector of FIG. 2 along the line C-C.
Figure 4:
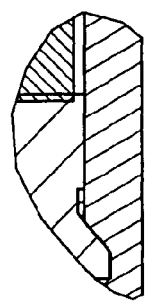
FIG. 4 shows the detail A from FIG. 2 in an enlarged illustration.

In order to secure the lower subsection 4 in the upper subsection 5 of the connecting part 2 against twisting, the lower subsection 4 has external teeth 56 above the encircling extension 8 and the upper subsection 5 has a corresponding internal teeth 58, as shown in FIG. 3. The internal teeth 58 and external teeth 56 engage one inside the other when the two parts are joined together.

To inject an active substance, the break-off part 20 of the connector 1 is twisted off or broken off by rotation or breaking, thereby exposing the self-sealing membrane 12. A conventional Luer lock syringe is then screwed to the connector 1.

FIG. 6 shows the connector 1 with the break-off part 20 broken off. A Luer lock syringe 28 has been screwed onto the connector 1, thus producing a liquid connection between the syringe 28 and the connector 1. Screwing in the syringe 28 pushes the front end of a tapered shaft 29 of the syringe 28 onto the trough-shaped depression 16 in the plate-like portion 14 of the membrane 12.

As the syringe 28 is being screwed on, the tapered shaft 29 advances further. Eventually, the tapered shaft 29 presses the upper, plate-like portion 14 of the membrane 12 downward. As a result, the lower side of the membrane 12 pushes onto the point 23 of the cannula 22.

Further screwing of the syringe 28 advances the tapered shaft 29 even further until eventually the cannula 22 pierces the pre-slit membrane 12 and penetrates a second cylindrical recess 30, which is a recess in the tapered shaft 29. When the syringe 28 has been completely screwed on, a narrow gap 31 remains between the tapered shaft 29 of the syringe 28 and the disk-shaped body 24 of the lower subsection 4 of the connecting part 2.

Unscrewing the syringe 28 pulls the tapered shaft 29 back again. As a result, the upper, plate-like portion 14 of the membrane 12 returns to its starting position and securely closes the connector 1. Since the membrane 12 is pre-slit, the point 23 of the cannula 22 penetrates the membrane 12 without damaging it. This ensures that the membrane 12 closes the connector 1 tightly again when the syringe 28 is unscrewed.

FIG. 7 shows a portion of an infusion or transfusion bag 32 together with the connector 1. The bag 32 consists of first and second film layers 32A and 32B that are welded to each other at to form a common edge 32C. The connector 1 is welded into an upper edge of the bag 32. The lower subsection 4 of the connecting part 2 of the connector 1 is pushed into a connecting piece 32D and is welded to the connecting piece 32D during the sterilization operation. Prior to assembling the connector 1, the bag 32 can not only be filled with a transfusion or infusion solution, it can also be filled with an enteral nutrient solution via the bores 25 in the lower subsection 4 of the connecting part 2 when the lower and upper subsections 4, 5 are not yet connected to each other.

Further exemplary embodiments of the connector according to the invention are described below. The main difference between these embodiments and the connector 1 described with reference to FIGS. 1 to 6 is that the connecting part differs in design. Unlike the connector 1 from FIGS. 1 to 6, which is intended for connection to a bag, the connectors described below are intended for connection to a bottle or tubing. Since the individual connectors differ only by the design of the connecting part 2, and in particular of the lower portion 6 of the lower subsection 4 of the connecting part 2, only the differences over the first exemplary embodiment of the connector 1 are described below. The mutually corresponding parts are provided with the same reference numbers in the figures.

Figure 8:
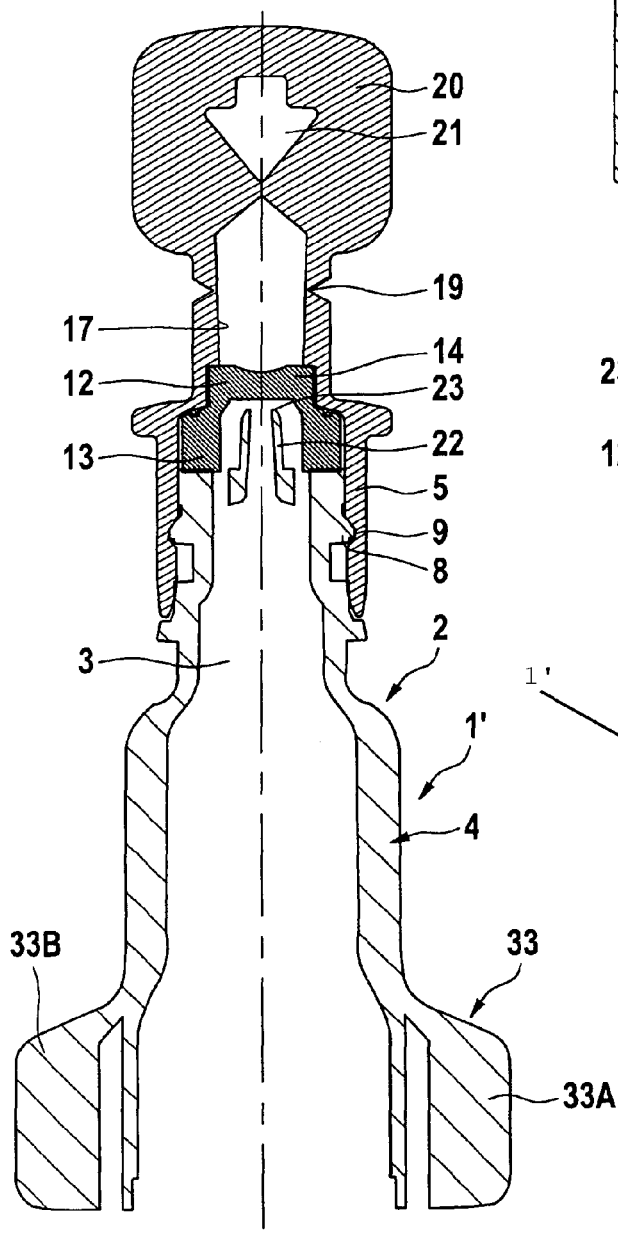
FIG. 8 shows a section through a second exemplary embodiment of the connector according to the invention.
Figure 9:
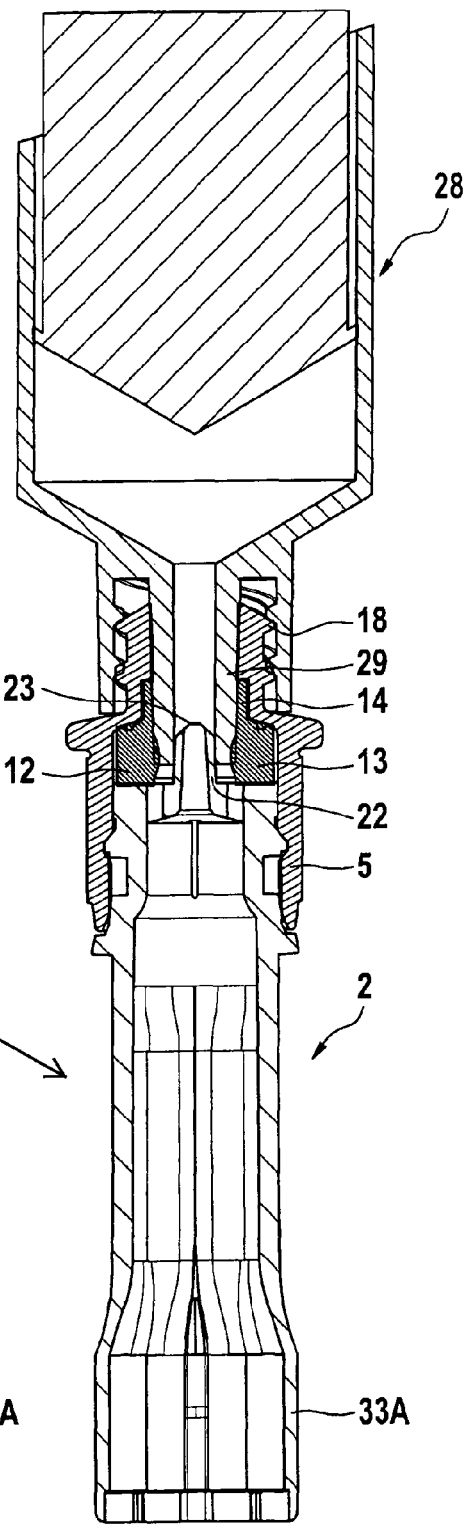
FIG. 9 shows the connector from FIG. 8 with the connected syringe in a sectioned illustration.

FIGS. 8 and 9 show sectional views of a first alternative connector 1'. In particular, FIG. 8 shows the first alternative connector 1' before connection of the syringe 28, and FIG. 9 shows the first alternative connector 1' after connection of the syringe 28.

In this first exemplary embodiment, a lower portion of a lower subsection 4 of the connector 1' is designed in the manner of a boat 33 that can be welded or adhesively bonded to a film bag. Boats of this type are known to a person skilled in the art to often be designed as flat bodies with a first lateral web 33A and a second lateral web 33B.

Figures 10, 11:
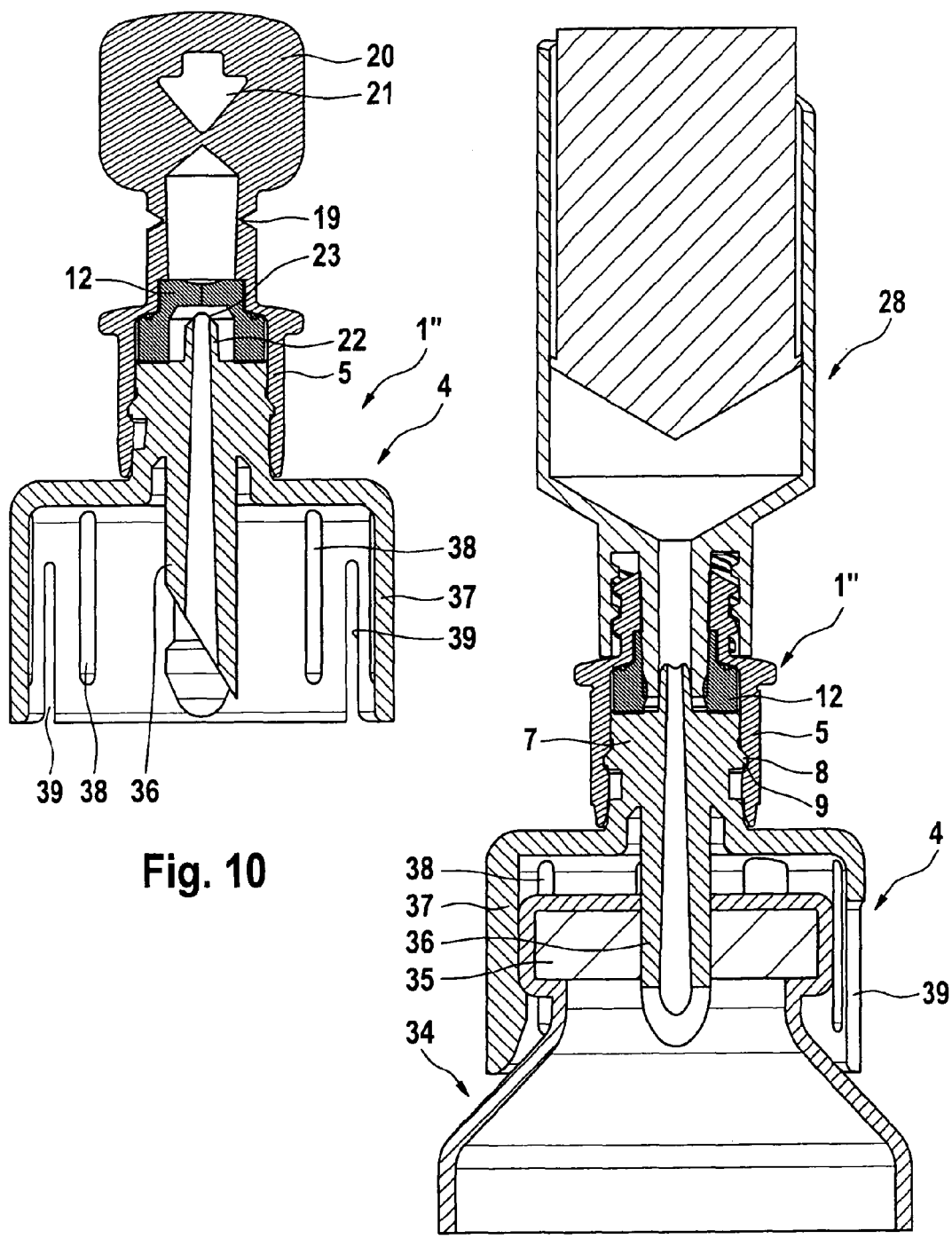
FIG. 10 shows a section through a third exemplary embodiment of the connector according to the invention.
FIG. 11 shows the connector from FIG. 10 with the connected syringe in a sectioned illustration.

FIGS. 10 and 11 show a second alternative connector 1" that is intended for connection to a bottle. In FIG. 10, the second alternative connector 1" is not yet connected to a bottle. FIG. 11 shows the second connector 1" shown in FIG. 10 but connected to a bottle 34. The bottle 34 is a conventional bottle for holding a medicinal liquid. A stopper 35 tightly closes the bottle 34.

The second alternative connector 1", which is designed as a connection adapter, has a spike 36 for piercing the stopper 35 of the bottle 34. The spike 36 extends downward from an upper, cylindrical portion 7 of the lower subsection 4 of the second alternative connector 1". A cylindrical subsection 37 surrounds the spike 36. The cylindrical subsection 37 is likewise integrally formed on the upper portion 7 of the lower subsection 4.

Inside the cylindrical subsection 37 are a plurality of webs 38 and a plurality of slits 39 such that the cylindrical subsection 37 can be placed onto the closure of the bottle 34. Such placement pierces the stopper 35, thus enabling withdrawal of liquid using the syringe 28.

Figure 12:
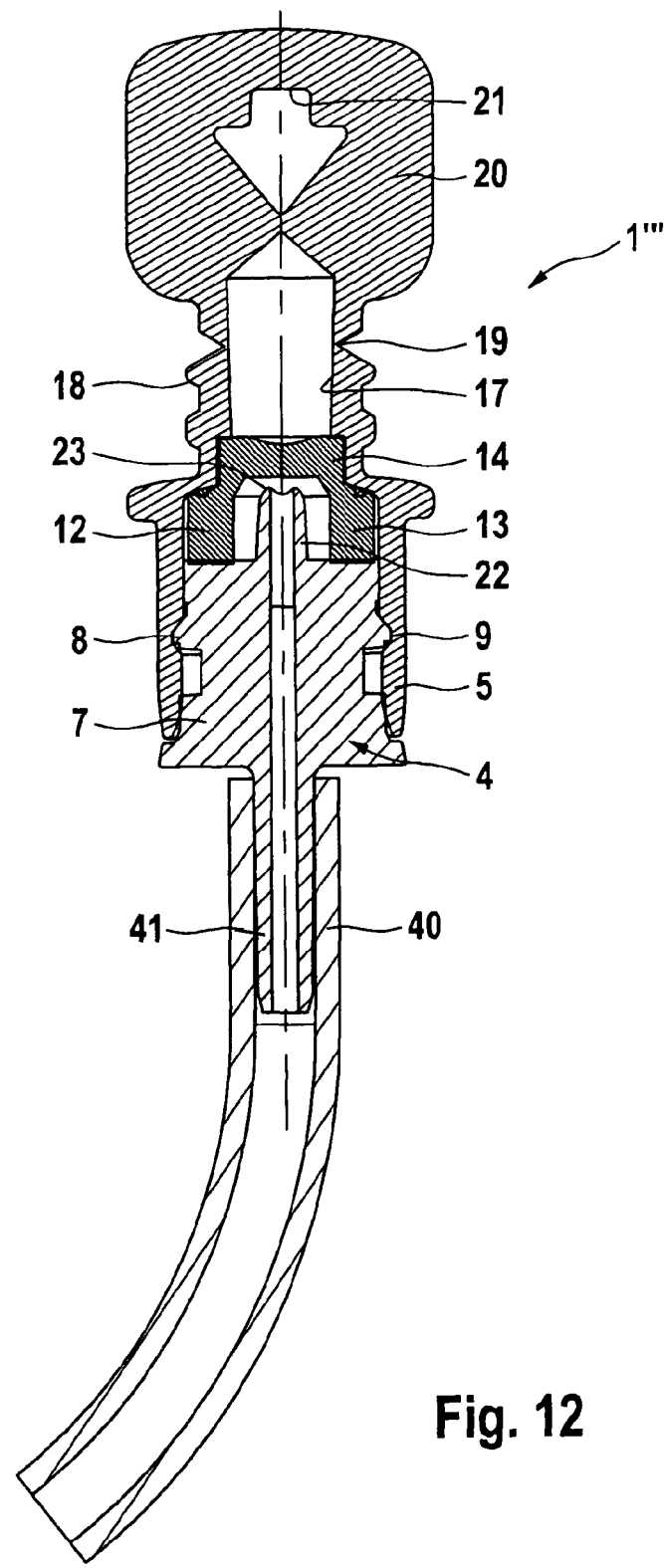
FIG. 12 shows a fourth exemplary embodiment of the connector.

A further exemplary embodiment, referred to herein as a third alternative connector 1''', is shown in FIG. 12. The third alternative connector 1''' is intended for connection to tubing 40, for example tubing for venous access. A lower portion 6 of a lower subsection 4 of the third alternative connector 1''' is designed as a hollow-cylindrical connecting piece 41 that is dimensioned in such a manner that the tubing 40 can be pushed onto the connecting piece 41 and can be welded or adhesively bonded to the connecting piece 41. Other than this, the third alternative connector 1''' of FIG. 12 does not differ in construction and manner of operation from the exemplary embodiments described above.

Figure 13:
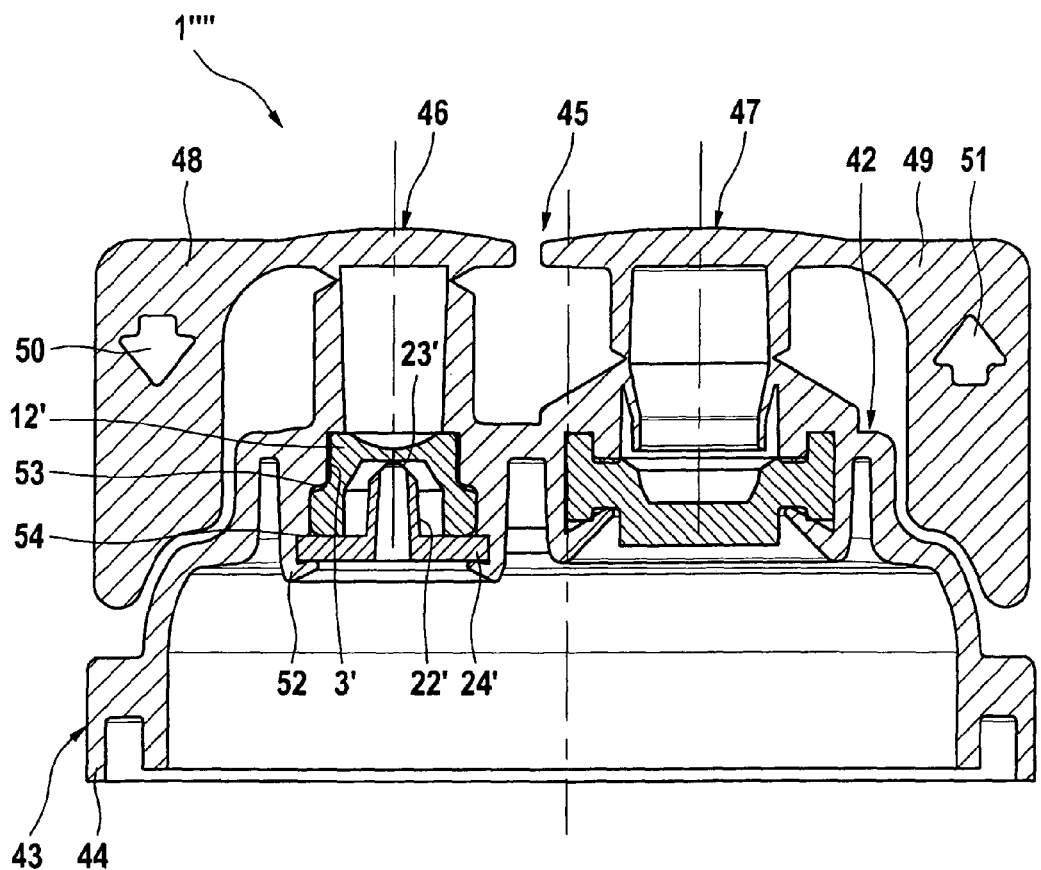
FIG. 13 shows a fifth exemplary embodiment of the connector.

FIG. 13 shows a fourth alternative connector 1''''. The fourth alternative connector 1'''' is designed as a closure cap for a bottle. The closure cap has a round cover part 42 that is adjoined by a cylindrical side part 43. A flange 44 for fastening the closure cap to a bottle head is situated on the lower edge of the side part 43.

The fourth alternative connector 1'''' has a port system 45 that comprises an injection point 46 for injecting liquid and a withdrawal point 47 for withdrawing liquid. The injection point 46 and the withdrawal point 47 are closed by corresponding first and second break-off parts 48, 49 that identify the two points of the port system as an injection part or withdrawal part by a respective first and second arrows 50, 51.

In this embodiment, the cover part 42 and the cylindrical side part 43 represent the connecting part 2 of the fourth alternative connector 1'''' that is placed onto the bottle (not illustrated in FIG. 13).

At the injection point 46, the round cover part 42 of the fourth alternative connector 1'''' has a recess 3'. A self-sealing membrane 12' is arranged in the recess 3'. It is this self-sealing membrane 12' that closes the recess 3'. The self-sealing membrane 12' is identical to the membrane 12 described with reference to the preceding exemplary embodiments.

In the embodiment of the fourth alternative connector 1'''', connecting a syringe 28 to the closure cap presses the membrane 12' onto a point of a hollow body 22' that is arranged below the membrane 12'. In the embodiment of the fourth alternative connector 1'''', the point 23' of the hollow body 22' is not, however, at a distance from the membrane 12'. Instead, the point 23' of the hollow body 22' is directly below the membrane 12'.

The hollow body 22' for piercing the membrane 12' upon connection of the syringe is integrally formed on a disk-shaped body 24' that sits together with the membrane 12' in the recess 3' of the cover part 42 of the closure cap. A projecting, encircling extension 52 that engages under the disk-shaped body 24' clamps the membrane 12', the hollow body 22', and the disk-shaped body 24' in the recess 3'. In this case, an upper projecting extension supports the lower portion of the membrane 12' in the recess 3' of the cover part 42 of the closure cap. Meanwhile, a lower-projecting extension 54 supports the disk-shaped body 24'. However, it is also possible to adhesively bond or to weld the disk-shaped body 24' to the cover part 42 of the closure cap. In this embodiment, the withdrawal point 47 of the closure cap does not have the connection according to the invention. Therefore, the withdrawal point of the closure cap is also not described in more detail.

The invention claimed is:

1. An apparatus comprising a connector for connecting a syringe to a container or tubing, wherein the connector comprises
    a connecting part having an upper end,
        wherein the connecting part is to be connected to the container or the tubing,
        wherein the connecting part has a recess in which a membrane is arranged;
    a break-off part that closes the recess of the connecting part and is connected to the upper end of the connecting part;
    wherein the break-off part comprises a tamper-evident closure, and a hollow body with a point that is arranged in the recess of the connecting part,
    wherein the membrane and the hollow body are arranged in the recess of the connecting part in such a manner that the membrane is pierced when the syringe is connected to the connecting part,
    wherein the membrane is arranged above the hollow body in the recess of the connecting part and therefore, when the syringe is connected to the connecting part, the membrane is pressed by the syringe onto the point of the hollow body, and
    wherein the membrane and the hollow body are arranged at a non-zero distance from each other in the recess of the connecting part,
    wherein the break-off part has an unbroken state and a broken state, wherein in the unbroken state the break-off part is an unbroken break-off part, wherein in the broken state the break-off part is a broken break-off part, wherein the break-off part is configured to transition from the unbroken state to the broken state, wherein a transition from the unbroken state to the broken state permits a liquid connection between the syringe and the connector.

2. The apparatus of claim 1, wherein the hollow body comprises a cannula that comprises a ground section.

3. The apparatus of claim 2, wherein the hollow body in the recess of the connecting part is fastened to a disk-shaped body that comprises openings.

4. The apparatus of claim 3, wherein the connecting part consists of a lower subsection and an upper subsection that are fixed by clicking into place, wherein the disk-shaped body is arranged at an upper end of the lower subsection.

5. The apparatus of claim 4, wherein the membrane has an upper, plate-like portion that is adjoined by an annular, lower portion.

6. The apparatus of claim 5, wherein the lower, annular portion of the membrane is held clamped between the lower subsection and the upper subsection of the connecting part.

7. The apparatus of claim 3, wherein the openings in the disk-shaped body comprise bores that are distributed circumferentially around the hollow body.

8. The apparatus of claim 4, wherein the membrane is held clamped between the lower subsection and the upper subsection of the connecting part.

9. The apparatus of claim 1, further comprising a container for medicinal liquids, wherein the connecting part of the connector is connected to the container.

10. The apparatus of claim 9, wherein the container comprises a bag, wherein the bag is selected from the group consisting of an infusion bag, a transfusion bag, and a bag for holding an enteral nutrient solution, wherein the connecting part of the connector comprises a closure part that is welded to the bag.

11. The apparatus of claim 9, wherein the container comprises a bag, wherein the bag is selected from the group consisting of an infusion bag, a transfusion bag, and a bag for holding an enteral nutrient solution, wherein the connecting part of the connector comprises a closure part that is adhesively bonded to the bag.

12. The apparatus of claim 1, wherein the membrane is slit in order to receive a tapered shaft of the syringe in a manner that maintains a seal around the tapered shaft of the syringe.

13. The apparatus of claim 1, wherein the connecting part has an external thread for the connection of a Luer Lock syringe.

14. The apparatus of claim 1, wherein an upper side of the membrane comprises a trough-shaped depression.

15. The apparatus of claim 1, wherein the break-off part as comprises a flat gripping piece that is connected to the upper end of the connecting part via an annular breaking zone.

16. The apparatus of claim 1, further comprising the syringe, wherein the syringe further comprises a tapered shaft.

17. The apparatus of claim 1, wherein the non-zero distance is sufficient to prevent unintentional piercing of the membrane.

18. The apparatus of claim 1, wherein the non-zero distance is selected to define a gap within the recess, wherein the gap within the recess extends across a portion of the recess that is between the hollow body and the membrane.

19. The apparatus of claim 1, wherein, as a result of having made a transition from the unbroken state to the broken state, the break-off part is precluded from making another transition from the unbroken state to the broken state.

* * * * *